(12) United States Patent
Dirac et al.

(10) Patent No.: US 8,449,772 B2
(45) Date of Patent: May 28, 2013

(54) MICRO FLUIDIC SYSTEM AND A METHOD OF ATTACHING A MEMBRANE TO A TUBE

(75) Inventors: Holger Dirac, Birkeroed (DK); Per Brandt Rasmussen, Augustenborg (DK); Arne Briest, Karlsruhe (DE)

(73) Assignee: Flowsion ApS, Nordborg (DK)

( * ) Notice: Subject to any disclaimer, the term of this patent is extended or adjusted under 35 U.S.C. 154(b) by 988 days.

(21) Appl. No.: 12/064,483

(22) PCT Filed: Aug. 22, 2006

(86) PCT No.: PCT/DK2006/000455
§ 371 (c)(1),
(2), (4) Date: Aug. 21, 2008

(87) PCT Pub. No.: WO2007/022775
PCT Pub. Date: Mar. 1, 2007

(65) Prior Publication Data
US 2009/0218272 A1    Sep. 3, 2009

(30) Foreign Application Priority Data
Aug. 24, 2005 (DK) .................. 2005 01178

(51) Int. Cl.
*B01D 63/00* (2006.01)

(52) U.S. Cl.
USPC ........... 210/321.89; 210/321.64; 210/321.79; 210/321.8; 210/321.88; 210/500.21; 210/500.23; 210/500.26

(58) Field of Classification Search
USPC ............. 210/244, 321.6, 321.64, 321.78, 210/321.79, 321.8, 321.87, 321.88, 321.89, 500.21, 500.23, 500.26; 29/890.1
See application file for complete search history.

(56) References Cited

U.S. PATENT DOCUMENTS 3,526,001 A * 8/1970 Smith .......................... 210/654
4,352,736 A * 10/1982 Ukai et al. ................ 210/321.88
(Continued)

FOREIGN PATENT DOCUMENTS

GB           994077           6/1965
WO         03000129           1/2003
(Continued)

OTHER PUBLICATIONS

International Search Report dated Apr. 1, 2007.

*Primary Examiner* — John Kim
(74) *Attorney, Agent, or Firm* — McCormick, Paulding & Huber LLP

(57) ABSTRACT

A micro fluidic system comprising at least one tube (1), a membrane (3) and at least one fitting member (4). The fitting member (4) is positioned around the membrane (3) and an end part (2) of the tube(s) (1), thereby fitting the membrane (3) to the end part(s) (2). The fitting member(s) (4) is/are made from a shrinkable material, and it/they is/are fitted tightly around the membrane (3) end part(s) (2). This is obtained by causing the shrinkable material to shrink, e.g. by heating the material, while the fitting member (4) is positioned around the membrane (3) and the end part(s) (2). It is an advantage that the fitting member (4) is made from a shrinkable material because this provides the possibility of fitting the membrane (3) tightly to the end part(s) (2) in an easy and cost effective manner. The micro fluidic system is very suitable for use in a probe, such as a dialysis probe. Also claimed is a method of manufacturing the micro fluidic system.

14 Claims, 2 Drawing Sheets

| U.S. PATENT DOCUMENTS | | | |
|---|---|---|---|
| 4,935,140 A | 6/1990 | Konstatin et al. | |
| 5,106,365 A | 4/1992 | Hernandez | |
| 5,145,583 A | 9/1992 | Angleraud et al. | |
| 5,607,390 A | 3/1997 | Patsalos et al. | |
| 2001/0015253 A1 | 8/2001 | Liska et al. | |
| 2005/0251087 A1 | 11/2005 | Carr et al. | |
| 2009/0218272 A1* | 9/2009 | Dirac et al. | 210/244 |

| FOREIGN PATENT DOCUMENTS | | |
|---|---|---|
| WO | 03000129 A2 | 1/2003 |
| WO | 03055540 | 7/2003 |
| WO | 03055540 A1 | 7/2003 |
| WO | 2005/032330 A2 | 4/2005 |
| WO | 2005032330 | 4/2005 |

* cited by examiner

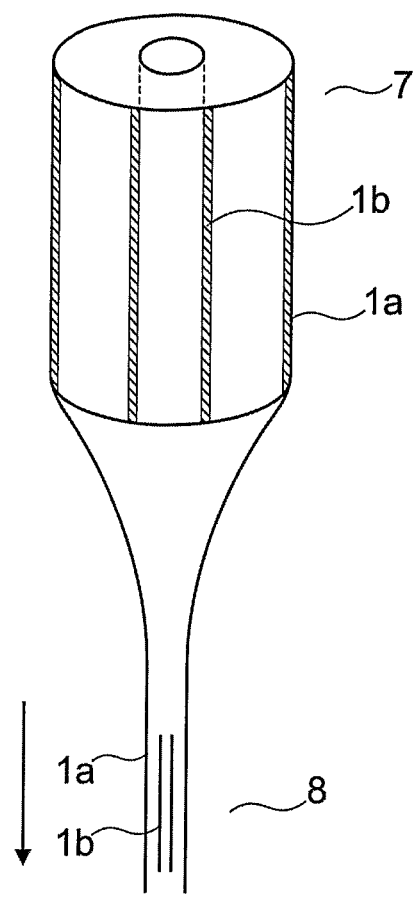
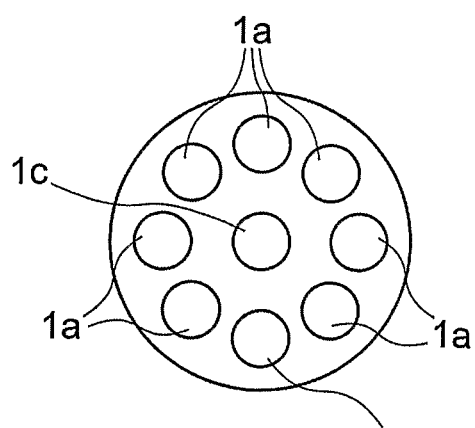
Fig. 4
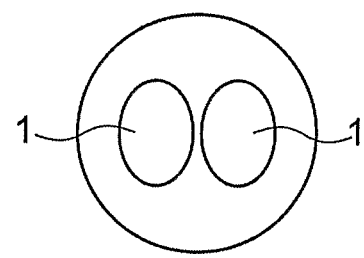
Fig. 5
Fig. 6

MICRO FLUIDIC SYSTEM AND A METHOD OF ATTACHING A MEMBRANE TO A TUBE

CROSS REFERENCE TO RELATED APPLICATIONS

This application is entitled to the benefit of and incorporates by reference essential subject matter disclosed in International Patent Application No. PCT/DK2006/000455 filed on Aug. 22, 2006 and Danish Patent Application No. PA 2005 01178 filed Aug. 24, 2005.

FIELD OF THE INVENTION

The present invention relates to a micro fluidic system having a membrane which is attached to a tube, in particular a capillary tube. The present invention further relates to a method of attaching a membrane to a tube, in particular a capillary tube.

BACKGROUND OF THE INVENTION

Micro fluidic systems in which a semi-permeable membrane is attached to one or more tubes are known per se. Such systems are, e.g., used in dialysis probes. Previously the membrane has been attached to the tube(s) by means of welding, melting or gluing the membrane to the tube(s). This is disadvantageous because it is relatively difficult, and thereby relatively expensive, to produce the micro fluidic systems in this manner.

SUMMARY OF THE INVENTION

It is, thus, an object of the present invention to provide a micro fluidic system which is easier to manufacture than the prior art micro fluidic systems.

It is a further object of the present invention to provide a micro fluidic system which is more cost effective to manufacture than prior art micro fluidic systems.

It is an even further object of the invention to provide a method for attaching a membrane to a tube in an easy and cost effective manner.

It is an even further object of the invention to provide a probe which is easy and cost effective to manufacture.

According to a first aspect of the invention the above and other objects are fulfilled by providing a micro fluidic system comprising:
- at least one tube,
- a membrane,
- at least one fitting member positioned around the membrane and an end part of the tube(s), thereby fitting said membrane to said end part(s), wherein the fitting member(s) is/are made from a shrinkable material, and wherein the fitting member(s) is/are fitted tightly around the membrane and the end part(s).

In the present context the term 'micro fluidic system' should be interpreted to mean a system having dimensions which are sufficiently small to at least substantially prevent turbulence in a fluid flowing in the system.

In the present context the term 'shrinkable material' should be interpreted to mean a material with the property that at least one dimension of an object made from the material decreases in response to the influence of an outer action, e.g. heat. This outer action should preferably be controllable, whereby the size of an object made from the material will be controllable.

The fitting member is fitted tightly around the membrane and the end part(s). This should be interpreted in such a way that the junction between the membrane and the end part(s) should be at least as tight as the membrane itself. Thus, it should preferably not be possible for substances which can not pass the membrane to pass between the membrane and the end part(s) at the position of the fitting member.

It is an advantage that the fitting member(s) is/are made from a shrinkable material because this provides the possibility of fitting the membrane tightly to the end part(s) of the tube(s) by means of shrinking the fitting member(s). This is a very easy manner of attaching the membrane to the tube(s), and the manufacture of the micro fluidic system is thereby easier and more cost effective than the manufacture of prior art micro fluidic systems.

The membrane may be semi-permeable, i.e. it may allow some substances to pass while other substances are not allowed to pass. The membrane may, e.g., comprise a polymer, such as a polyether-polycarbonate block copolymer. The membrane may, e.g., be based on polyvinylidene fluoride (PVDF) and a hydrophilic polymer, such as copolymers of acrylonitrile or monomers containing sulphonic groups. Such membranes are commercially available, and examples of such membranes can, e.g., be found in U.S. Pat. Nos. 4,935,140 and in 5,145,583.

The membrane may be a dialysis membrane. Such membranes are typically permeable to specific substances or particles, e.g. glucose, present in a body fluid, typically blood. However, the membrane is typically not permeable to perfusion liquid flowing in the interior of the micro fluidic system. The perfusion liquid may, e.g., be or comprise a isotonic saline solution.

In one embodiment the micro fluidic system may comprise two or more tubes. At least two of the tubes may be arranged parallelly, e.g. co-axially, i.e. with one tube inside the other. Alternatively two or more tubes may be arranged side-by-side, e.g. with one centre tube and a number of tubes arranged circularly around the centre tube. The two or more tubes may thereby form a so-called multi-lumen tube.

Alternatively or additionally, at least two of the tubes may be arranged at least substantially along a common axis and with their end parts facing each other. In this embodiment the membrane preferably connects the two end parts facing each other along the common axis.

Alternatively, the micro fluidic system may comprise only one tube with the membrane attached thereto.

In one embodiment the tube(s) may be capillary tube(s), such as glass capillary tubes. In the present context the term 'capillary tube' should be interpreted as a tube with inner dimensions which allow a capillary effect to occur when the tube is used in combination with a predefined fluid.

Preferably, a transversal dimension for at least one of the capillary tube(s) is within the interval 0.5 µm to 500 µm, such as within the interval 1 µm to 200 µm, such as within the interval 50 µm to 100 µm.

The fitting member(s) is/are preferably made from a heat shrinkable material, i.e. from a material which is shrinkable in response to heating the material to a temperature within a specific temperature interval. This will be described further below. The heat shrinkable material may, e.g., be or comprise polyethylene. An example of such a material is UL 224, MIL-I-23053/5, which is a highly flexible material with a shrinking temperature of approximately 120° C. When subjected to heat, a tube made from this material will shrink to approximately half the original diameter. Another example of a heat shrinkable material is 'Krympeflex'. This material shrinks when it is heated to a temperature within the temperature interval 120° C. to 200° C.

The micro fluidic system may further comprise a substantially rigid hood positioned at or near the end part(s) and between the tube(s) and the membrane. Such a substantially rigid hood may help in defining a cavity between the membrane and the tubes. This is advantageous in case the micro fluidic system is to form part of a probe, such as a dialysis probe.

The membrane may be shaped with one closed end and one open end. In this case the open end will be slid over the end part(s) and attached thereto by means of one fitting member. Alternatively, the membrane may be shaped as a tube, i.e. with two open ends. In this case both ends of the membrane will need to be fitted to the end part(s) by means of a fitting member. However, since the process of fitting the membrane to the end part(s) by shrinking the fitting member(s) is relatively easy, this is not a big disadvantage. On the other hand, the tube-shaped membranes can easily be mass produced by simply cutting them in a desired length from very long tubes of membrane material. Therefore this embodiment is very advantageous, since the advantages arising from the easy manufacture of the membrane by far exceeds the minor disadvantages arising in connection with the attaching procedure.

According to a second aspect of the invention the above and other objects are fulfilled by providing a probe comprising a micro fluidic system according to the first aspect of the invention. Such a probe will be easier, and thereby more cost effective, to manufacture than similar prior art probes.

The probe may preferably be a multi-lumen probe, i.e. a probe comprising two or more tubes in which fluid may flow.

The probe may be a dialysis probe, such as a micro dialysis probe. In this case, and in case the probe is a multi-lumen probe, perfusion liquid will typically flow through some of the tubes towards the membrane region where it will collect substances or particles (e.g. glucose) from a body fluid, e.g. blood, in which the probe is inserted. The perfusion liquid, as well as the collected substances or particles, will subsequently flow away from the membrane region along the remaining tubes.

According to a third aspect of the invention the above and other objects are fulfilled by providing a method of attaching a membrane to a tube, the method comprising the steps of:
    providing a tube having an end part,
    positioning a membrane at said end part of said tube,
    positioning a fitting member around the membrane and the end part, said fitting member being made from a shrinkable material, and
    shrinking said fitting member, thereby providing a tight fit between the tube, the membrane and the fitting member.

It should be noted than any feature described in combination with the first aspect of the invention may also be combined with the second or third aspects of the invention, any feature described in combination with the second aspect of the invention may also be combined with the first and third aspects of the invention, and any feature described in combination with the third aspect may also be combined with the first and second aspects of the invention.

As described above, it is an advantage that the fitting member is fitted to the membrane and the end part(s) by shrinking because this provides an easy and cost effective manner of attaching the membrane to the tube(s).

The step of shrinking the fitting member may comprise heating at least the fitting member to a predefined temperature. The predefined temperature will, of course, depend on the material of the fitting member. However, the temperature should be sufficient to cause the fitting member to shrink. Furthermore, the temperature should not be so high that permanent damage is caused to the fitting member and/or to other parts, such as the membrane or tube(s). This is an advantageous embodiment because the fitting member(s) in this case is/are fitted tightly to the membrane and the end part(s), simply by subjecting at least the fitting member(s) to heat. This is much easier than melting, welding or gluing the membrane to the end part(s).

In one embodiment the step of shrinking the fitting member may comprise heating at least the fitting member to a temperature with the interval 80° C. to 300° C., such as within the interval 100° C. to 250° C., such as within the interval 120° C. to 200° C. As described above, the material 'Krympeflex' will shrink when heated to a temperature within the interval 120° C. to 200° C.

The method may further comprise the step of removing part of said tube prior to the step of positioning the membrane, thereby forming a cavity between the remaining part of the tube and the membrane. In case the resulting tube(s)/membrane forms part of a probe, such as a dialysis probe, perfusion liquid can flow towards the cavity where it will remain for a while collecting substances or particles which have penetrated the membrane. The perfusion liquid will subsequently flow away from the cavity along with the collected substances or particles. This has already been described above. The cavity will increase the contact volume between the perfusion liquid and the substances or particles, thereby improving the collection of these.

The step of providing a tube may comprise providing a capillary tube. This has already been described above.

A capillary tube may be provided in the following manner. Initially, a desired configuration of glass tubes is formed. This may, e.g. be just a single tube, two or more tubes arranged side-by-side, two or more tubes arranged co-axially, a centre tube surrounded by a number of tubes arranged in a circular pattern, or any other desired configuration. Subsequently the tube(s) may be heated and simultaneously pulled along an axial direction. As a consequence, the dimension of the tubes is increased along the axial direction while it is decreased along a transversal direction. However, the desired configuration is maintained. Thereby very thin tubes, preferably capillary tubes, are formed. This method is very similar to the method which is used when manufacturing optical fibres.

BRIEF DESCRIPTION OF THE DRAWINGS

The invention will now be further described with reference to the accompanying drawings in which:

FIG. 4 shows a multi-lumen tube during its manufacturing, FIG. 5 shows one arrangement of tubes in a multi-lumen probe, and FIG. 6 shows an alternative arrangement of tubes in a multi-lumen probe.

DETAILED DESCRIPTION OF THE PREFERRED EMBODIMENTS

Figure 1:
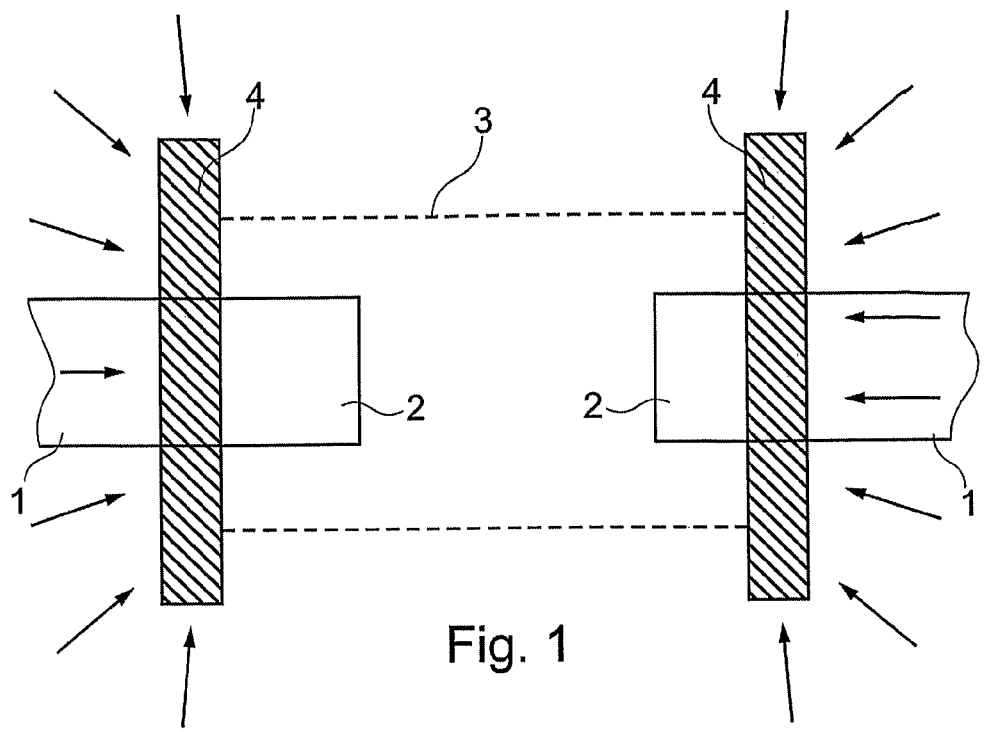
FIG. 1 shows a micro fluidic system according to one embodiment of the invention and having two tubes with end parts facing each other before shrinking the fitting members.

FIG. 1 shows a micro fluidic system according to one embodiment of the invention. The micro fluidic system comprises two tubes 1, each having an end part 2. The end parts 2 of the two tubes 1 are facing each other, and the tubes 1 are arranges substantially along a common longitudinal axis. The micro fluidic system further comprises a semi-permeable membrane 3 which is arranged in such a way that both of the end parts 2 are positioned in an interior part of the membrane 3.

Enclosing the membrane 3 and the end parts 2 are two fitting members 4. The fitting members 4 are made from a shrinkable material, i.e. their dimensions may be decreased. However, FIG. 1 shows the micro fluidic system prior to shrinking the fitting members 4, and the fitting members 4 are therefore not fitted tightly to the membrane 3 and the tubes 1. This makes it very easy to position the membrane 3 and the fitting members 4 around the end parts 2.

Figure 2:
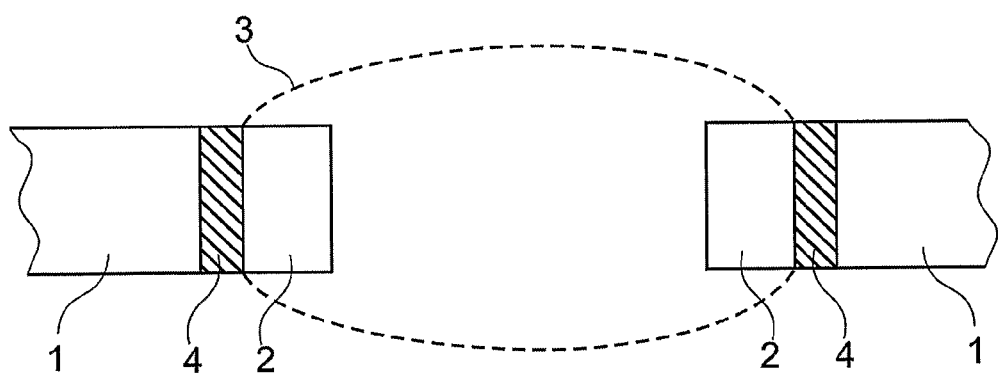
FIG. 2 shows the micro fluidic system of FIG. 1 after shrinking the fitting members.

FIG. 2 shows the micro fluidic system of FIG. 1. However, in FIG. 2 the fitting members 4 have been caused to shrink, preferably by heating the fitting members 4. As it is clear from FIG. 2 the fitting members 4 are now fitted tightly around the membrane 3 and the end parts 2.

Figure 3:
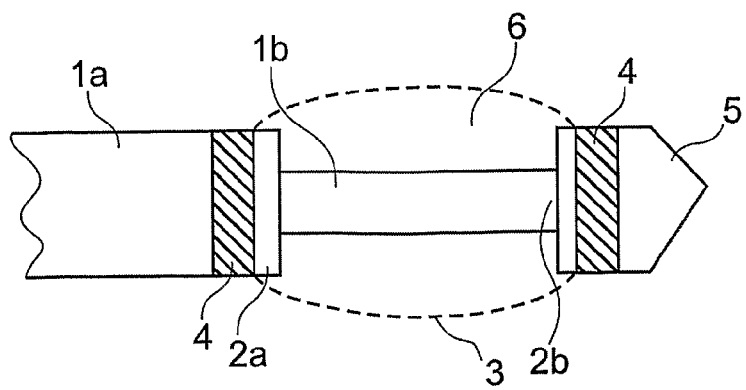
FIG. 3 shows a micro fluidic system according to another embodiment of the invention in the form of a multi-lumen probe.

FIG. 3 shows a micro fluidic system according to another embodiment of the invention. The micro fluidic system of FIG. 3 comprises two tubes 1 arranged co-axially. A part of the outer tube 1a has been removed, thereby exposing the inner tube 1b. The micro fluidic system is further provided with a rigid hood 5 positioned near the end part 2b of the inner tube 1b. Between the end parts 2 of the tubes 1a membrane 3 is attached by means of two fitting members 4 which have been subject to shrinking as described above. Due to the fact that part of the outer tube 1a has been removed, a cavity 6 is formed between the membrane 3 and the inner tube 1b. The rigid hood 5 is used for stabilising the micro fluidic system as well as for attaching the membrane 3 by means of the fitting members 4.

FIG. 4 shows a multi-lumen tube during its manufacturing. A part of the tube has been broken away for clarity. The tube comprises an outer tube 1a and an inner tube 1b. The outer tube 1a and the inner tube 1b are arranged co-axially. Initially a tube as shown in the upper part 7 of the Figure is made. Thereby a desired mutual position of the outer tube 1a and the inner tube 1b is established. Subsequently the tube is pulled, while heating the tube, along an axial direction indicated by the arrow. Thereby a narrow tube with the same mutual position of the outer tube 1a and the inner tube 1b is obtained, as shown in the lower part 8 of the Figure.

FIG. 5 shows one arrangement of tubes 1 in a multi-lumen probe. The tubes are arranged with a centre tube 1c surrounded by seven outer tubes 1a arranged in a circular pattern.

FIG. 6 shows an alternative arrangement of tubes 1 in a multi-lumen probe. In FIG. 6 two tubes 1 are arranged parallelly side-by-side.

While the present invention has been illustrated and described with respect to a particular embodiment thereof, it should be appreciated by those of ordinary skill in the art that various modifications to this invention may be made without departing from the spirit and scope of the present invention.

What is claimed is:

1. A micro fluidic system comprising:
    a single multi-lumen tube defining two or more lumens substantially parallelly arranged side-by-side, the single multi-lumen tube defining a reduced portion;
    a semi-permeable dialysis membrane positioned over the reduced portion of the single multi-lumen tube;
    at least one fitting member positioned around the semi-permeable dialysis membrane and a portion of the single multi-lumen tube, thereby fitting the semi-permeable dialysis membrane to said portion of the single multi-lumen tube;
    wherein the fitting member(s) is/are made from a shrinkable material, and wherein the fitting member(s) is/are fitted tightly around the semi-permeable dialysis membrane and the portion of the single multi-lumen tube where the membrane is fitted;
    wherein a cavity is formed between the reduced portion of the single multi-lumen tube and the semi-permeable dialysis membrane.

2. The micro fluidic system according to claim 1, wherein at least two of the lumens are arranged at least substantially along a common axis and with their end parts facing each other.

3. The micro fluidic system according to claim 1, wherein the lumens are capillary tubes.

4. The micro fluidic system according to claim 3, wherein at least one of the capillary tubes is a glass capillary tube.

5. The micro fluidic system according to claim 3, wherein a transversal dimension for at least one of the capillary tube(s) is within the interval 0.5 μm to 500 μm.

6. The micro fluidic system according to claim 1, further comprising a substantially rigid hood positioned at or near an end part of the single multi-lumen tube, wherein the semi-permeable dialysis membrane is disposed between the end part of the single multi-lumen tube and the hood.

7. A probe comprising the microfluidic system according to claim 1.

8. The probe according to claim 7, wherein the probe is a multi-lumen probe.

9. The probe according to claim 7, wherein the probe is a dialysis probe.

10. A method of attaching a membrane to a tube, the method comprising the steps of:
    providing a single multi-lumen tube defining two or more lumens substantially parallelly arranged side-by-side, the single multi-lumen tube having an end part;
    removing an outer portion of the single multi-lumen tube to define a reduced portion in the single multi-lumen tube;
    positioning a semi-permeable membrane at said end part of said single multi-lumen tube and over the reduced portion of the single multi-lumen tube, thereby forming a cavity between the reduced portion of the single multi-lumen tube and the semi-permeable membrane;
    positioning a fitting member around the semi-permeable membrane and the end part of the single multi-lumen tube, said fitting member being made from a shrinkable material; and
    shrinking said fitting member, thereby providing a tight fit between the end part of the single multi-lumen tube, the semi-permeable membrane and the fitting member.

11. The method according to claim 10, wherein the step of shrinking the fitting member comprises heating at least the fitting member to a predefined temperature.

12. The method according to claim 11, wherein the step of shrinking the fitting member comprises heating at least the fitting member to a temperature with the interval 80° C. to 300° C.

13. The method according to claim 10, wherein the step of providing a single multi-lumen tube comprises providing a capillary tube.

14. A micro fluidic system prepared by a process comprising the steps of:
    providing two or more tubes substantially parallelly arranged side-by-side;

simultaneously heating and stretching in an axial direction the two or more tubes to produce a single multi-lumen tube defining two or more lumens substantially parallelly arranged side-by-side;

removing an outer portion of the single multi-lumen tube that defines at least one of the two or more lumens to produce a reduced portion in the single multi-lumen tube;

positioning a semi-permeable membrane at said end part of said single multi-lumen tube and over the reduced portion of the single multi-lumen tube, thereby forming a cavity between the reduced portion of the single multi-lumen tube and the semi-permeable membrane;

positioning a fitting member around the semi-permeable membrane and the end part of the single multi-lumen tube, said fitting member being made from a shrinkable material; and shrinking said fitting member, thereby providing a tight fit between the end part of the single multi-lumen tube, the semi-permeable membrane and the fitting member.

* * * * *